(12) United States Patent
Wu et al.

(10) Patent No.: US 6,746,862 B1
(45) Date of Patent: Jun. 8, 2004

(54) METHOD FOR CULTIVATION OF FILAMENTOUS FUNGI

(75) Inventors: Wen-Teng Wu, Hsinchu (TW); Pei-Ming Wang, Kaohsiung (TW); Ting-Kuo Huang, Chang-He (TW); Gwo-Fang Yuan, Hsinchu (TW)

(73) Assignee: Food Industry Research & Development Institute, Hsinchu (TW)

( * ) Notice: Subject to any disclaimer, the term of this patent is extended or adjusted under 35 U.S.C. 154(b) by 0 days.

(21) Appl. No.: 09/611,992

(22) Filed: Jul. 7, 2000

(30) Foreign Application Priority Data

Mar. 3, 2000 (TW) ........................................ 89103793 A

(51) Int. Cl.⁷ .................................................. C12N 1/14
(52) U.S. Cl. ................. 435/254.1; 435/171; 435/295.3; 424/195.15; 426/30
(58) Field of Search ........................... 435/295.2, 295.3, 435/171, 254.1, 71.1, 243, 431, 420, 41.1; 424/195.15; 426/30, 60; 47/1.1; 71/5

(56) References Cited

U.S. PATENT DOCUMENTS

| | | | | |
|---|---|---|---|---|
| 3,765,906 A | * | 10/1973 | Yamaguchi et al. | |
| 4,031,250 A | * | 6/1977 | Haas et al. | |
| 4,418,080 A | * | 11/1983 | Yueh et al. | |
| 4,954,440 A | * | 9/1990 | Johal et al. | |
| 5,013,655 A | * | 5/1991 | Bayer et al. | |
| 5,077,201 A | * | 12/1991 | Eyal et al. | |

OTHER PUBLICATIONS

"Suspended Rice Particles for Cultivation of *Monascus purpureus* in a Tower–type Bioreactor": Wu,WT et al: Applied MIcrobiology and Biotechnology, May 2000, Vol 53. No. 5. pp. 542–544.*
"An Airlift Reactor eith Double Net Draft Tubes and its Application in Fermentation": Tung et al: Bioprocess Engineering. 1997. vol. 17, No. 1, pp 1–5.*

* cited by examiner

Primary Examiner—Leon B. Lankford, Jr.
Assistant Examiner—Ruth A. Davis
(74) Attorney, Agent, or Firm—Fish & Richardson P.C.

(57) ABSTRACT

The invention discloses a method for cultivation of filamentous fungi using a suspended nutritionally solid substrate, the method including the steps of: (a) preparing a medium comprising a nutritionally solid substrate; and (b) inoculating an inoculum into the medium comprising the nutritionally solid substrate in a bioreactor to carry out fermentation. The present invention combines the properties of solid-state culture and submerged culture. In addition, the present invention may employ an air-lift bioreactor with a net draft tube and the fed-batch process to elevate the yields of filamentous fungi and metabolites thereof.

23 Claims, 6 Drawing Sheets

METHOD FOR CULTIVATION OF FILAMENTOUS FUNGI

BACKGROUND OF THE INVENTION

1. Field of the Invention

The present invention relates to a method for cultivation of filamentous fungi, and more particularly to a method for cultivation of filamentous fungi by using suspended nutritionally solid substrates.

2. Description of the Related Arts

Generally, the method for fermentation of filamentous fungi can include the use of solid-state culture or submerged culture. The conventional method for the most part uses solid-state culture. One example of producing metabolites from Monascus species is directly inoculating Monascus species into solid nutritional medium such as grain medium, for example rice or wheat. Then, fermentation is carried out. The mycelia of Monascus species penetrate into the surface of the solid nutritional medium and grow during the period of fermentation. The pigments produced are absorbed so that the color of the medium turns purple. In addition, the mycelia also penetrate inside the grain particles. This phenomenon facilitates the production of pigments. In 1991, Johns and Stuar employed Carrageenan particles consisting of synthetic medium to simulate grain in culture (Johns and Stuar, (1991) *J. Industrial Microbiology,* 8:23–28). However, due to reasons such as structure, nutrition components, etc, the synthetic medium is not suitable for Monascus species in the production based on solid-state culture. Generally, to adequately make use of medium and maintain optimal temperature and humidity, the operation procedures of conventional solid-state culture are complex and time-consuming. Moreover, some problems such as the restriction of oxygen transfer, contamination, etc., also make the scale-up difficult.

Furthermore, because of the disadvantages of solid-state culture described above, the quality and quantity of the products are usually unstable. To solve this problem, many studies have developed submerged culture to carry out the fermentation. In 1982, Lin and Lizuka employed saccharide and cereal meals as a carbon source to solve the problems of scale-up and operation control (Lin and Lizuka, (1982)*Appl. Environ. Microbiology,* 43:671–676). However, the yield of the pigments is significantly reduced using this method. In 1984, Evans and Wang employed algin (an inert substance in which no nutrient is contained) to immobilize Monascus species and then carry out submerged culture. The result showed the phenomenon of mycelia attachment conduces the production of the pigments (Evans and Wang, (1984) *Applied and Environmental Microbiology* 47(6): 1323–1326). In 1990, Mak et. al. introduced roller bottle culture, which has the properties of high oxygen mass transfer and low shear stress to provide an environment for mycelia attachment, and used glucose as a carbon source to carry out the cultivation of Monascus species (Mak et. al., (1990) *Enzyme Microbiol. Technol.,* 12:965–968). However, due to the nature of the roller bottle, the scale of the production is too small using this method. In 1995, Lee et. al. used topioca starch as a carbon source and pointed out that a high initial starch concentration in the medium is not suitable for practical use due to high viscosity of the medium (Lee et. al., (1995) *J. Fermentation of Bioengineering,* 79(5): 516–518). They proposed a solid-liquid state culture with gelatinized starch block provided at the bottom and a dilute soluble starch at the upper part of the reactor. The cultivation was carried out in a stirred-tank bioreactor. However, their proposed approach might have scale-up problem since the interface area to volume ratio is small for a large-scale system.

These examples of submerged culture of filamentous fungi use nutritional medium such as algin and tapioca starch. All show poor fermentation yields.

Thus, the primary object of the present invention aims to improve the poor fermentation yields described above.

In addition, another object of the present invention is to carry out the submerged culture under the conditions of mycelia attachment and to avoid destroying mycelia and the attached material by the shear stress of the bioreactor, thus improving the process of producing filamentous fungi and to scale up the production of metabolites.

SUMMARY OF THE INVENTION

It is therefore an object of the present invention to provide a method for cultivation of filamentous fungi such as Monascus species by using a suspended nutritionally solid substrate, the method comprising the steps of: (a) preparing a medium comprising the nutritionally solid substrate; and (b) inoculating an inoculum into the medium comprising the nutritionally solid substrate in a bioreactor to carry out fermentation.

The method of the present invention can alternatively comprise a step of inoculating the filamentous fungi after step (a) to obtain an inoculum, then inoculating said inoculum into the medium comprising the nutritionally solid substrate in a bioreactor to carry out fermentation.

In the method according to the present invention, the bioreactor is a pneumatic bioreactor, more preferably an air-lift bioreactor with a net draft tube.

The method of the present invention can further comprise a step of cultivating the filamentous fungi using the fed-batch process, wherein the medium of the batch comprises a nitrogen source and the nutritionally solid substrate.

BRIEF DESCRIPTION OF THE DRAWINGS

The present invention will be more fully understood and further advantages will become apparent when reference is made to the following description of the invention and the accompanying drawings in which.

DETAILED DESCRIPTION OF THE INVENTION

Figure 1:
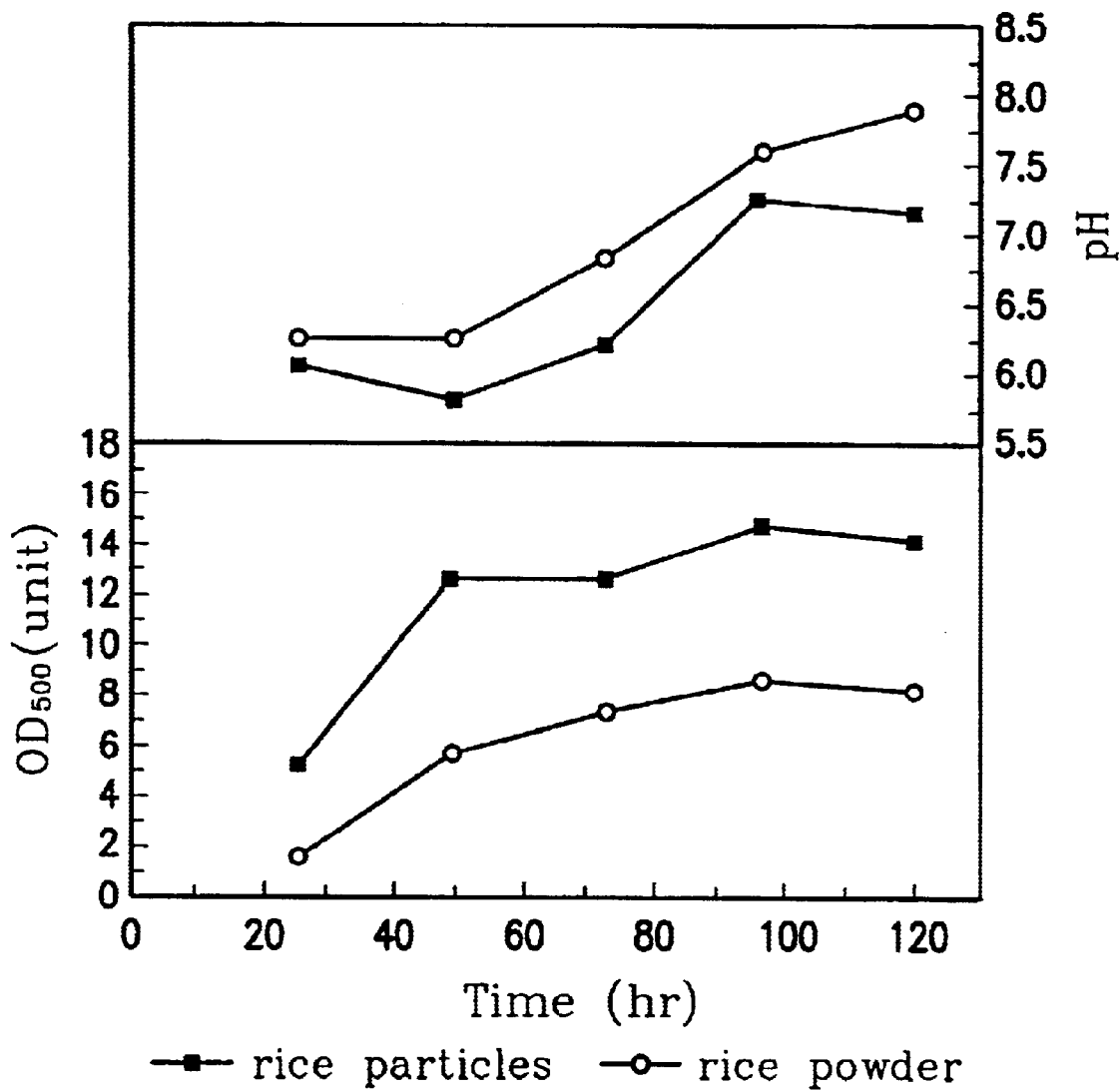
FIG. 1 is a diagram showing the time course of the cultivation of Monascus species and pigments produced by fermentation using different types of nutritional substrate.

In embodiment of the present invention described herein, the filamentous fungi used is Monascus. However, other filamentous fungi, such as Penicillium, Aspergillus, etc., with the similar growth properties are also suitable for the application of the present invention.

According to the present invention, the method for cultivation of filamentous fungi such as Monascus species by using a suspended nutritionally solid substrate comprises the following steps: (a) preparing a medium comprising the nutritionally solid substrate; and (b) inoculating an inoculum into the medium comprising the nutritionally solid substrate in a bioreactor to carry out fermentation.

The term "nutritional solid substrate" used herein is defined as a substrate which keeps its solid morphology in medium to provide a place where the mycelia can attach to, and to provide a carbon source required for the growth of the fungi. The carbon source can be, for example, carbohydrates. Suitable carbohydrates include, but are not limited to, rice, wheat and other grains. Prior to adding to the medium, the grain may be treated by the process of husking, cooking and sterilizing. Because the structure of the grain (e.g. rice or wheat) is very suitable for mycelia attachment, and grain can provide the major nutrition source for the fungi, the cultivation of the Monascus species of the present invention is carried out by using a medium comprising suspended nutritional solid substrate such as rice substrates, so that it can possess both the properties of mycelia attachment and suspended fluidity. carbohydrates. Suitable carbohydrate includes, but are not limited to, rice, wheat and other grains. Prior to adding to the medium, the grain may be treated by the process of husking, cooking and sterilizing. Because the structure of the grain (e.g, rice or wheat) is very suitable for mycelia attachment, and grain can provide the major nutrition source for the fungi, the cultivation of Monascus species of the present invention is carried out by using a medium comprising suspended nutritionally solid substrate such as rice substrates, so that it can possess both the properties of mycelia attachment and suspended fluidity.

The medium used in step (a) according to the present invention further comprises the components of a nitrogen source, inorganic salts and trace elements.

The present invention further comprises a step of inoculating the filamentous fungi after step (a) to obtain an inoculum, the method comprising the steps of: (1) inoculating said filamentous fungi from a stock culture to a new agar plate and incubating in an incubator for 5–7 days; (2) washing spores and mycelia grown on said plate with sterile water; (3) cultivating said spores/mycelia in a medium comprising a nutritionally solid substrate by shaking; and (4) inoculating a culture cultivated for 36–48 hours at step (3) into a bioreactor.

Bioreactors can be classified as pneumatic or stirred-tank according to the mixing system. The term "pneumatic bioreactor" means mixing air with medium by aerating, whereas the term "stirred-tank bioreactor" means mixing air with medium by stirring with a stirring wing. The "air-lift bioreactor" is a pneumatic bioreactor equipped with a draft tube, whereas the "air-lift bioreactor with double net draft tubes" is a pneumatic bioreactor equipped with a concentric double net draft tubes (an example is described later). To maintain the mycelia and nutritionally solid substrates intact and avoid the destructiveness of a large shear stress, the present invention uses the pneumatic bioreactor to cultivate Monascus species, preferably the air-lift bioreactor with double net draft tubes.

The method of the invention further comprises cultivating the filamentous fungi using the fed-batch process, wherein the medium of the batch comprises a nitrogen source and a nutritionally solid substrate described above.

Without intending to limit it in any manner, the present invention will be further illustrated by the following examples.

EXAMPLE 1
The Effect of Different Types of Nutritional Substrates Upon the Yield of the Pigment The M15 strain (Monascus purpureus, deposit number: CCRC 31615, Hsinchu, Taiwan) and Medium A (including 2% rice particles or 2% rice powder as the carbon source, 1.26% monosodium glutamate, 0.24% $KH_2PO_4$, 0.24% $K_2HPO_4$, 0.8% $MgSO_4.7H_2O$, 0.05% KCl, 0.001% $FeSO_4.7H_2O$, 0.001% $ZnSO_4.7H_2O$ and 0.0003% $MnSO_4.H_2O$) were employed for submerged culture.

Before shaken flask cultivation, Monascus was inoculated from a stock culture to a new medium plate containing 39 g/L of Potato-Dextrose Agar (PDA). The plate was incubated at 30° C. for 6 days. 6 ml of sterile water suspension from the 6-day-old PDA plate was used as seed for the preparation of inoculum. A 1 liter Erlenmeyer flask containing 300 ml of culture medium was inoculated with 3 ml of spore/mycelium suspension and incubated at 30° C. on a rotary shaker at 200 rpm. The 2-day-old culture broth was used as inoculum for the submerged cultivation. The pigments production was carried out in 1 liter shaken flasks, each containing 270 ml of culture medium and inoculated with 30 ml of mycelium broth. The flasks were incubated at 30° C. on rotary shaker at 200 rpm, and the yield of pigments was monitored. The result is shown in FIG. 1.

Result

The red pigments produced by using medium containing suspended rice particles were 2 fold higher than those produced by using medium containing rice powder. The reason might be the attachment of the fungi to the grains as in the solid-state culture.

EXAMPLE 2
The Effect of Inoculation Time Upon the Yield of the Pigment

Figure 2:
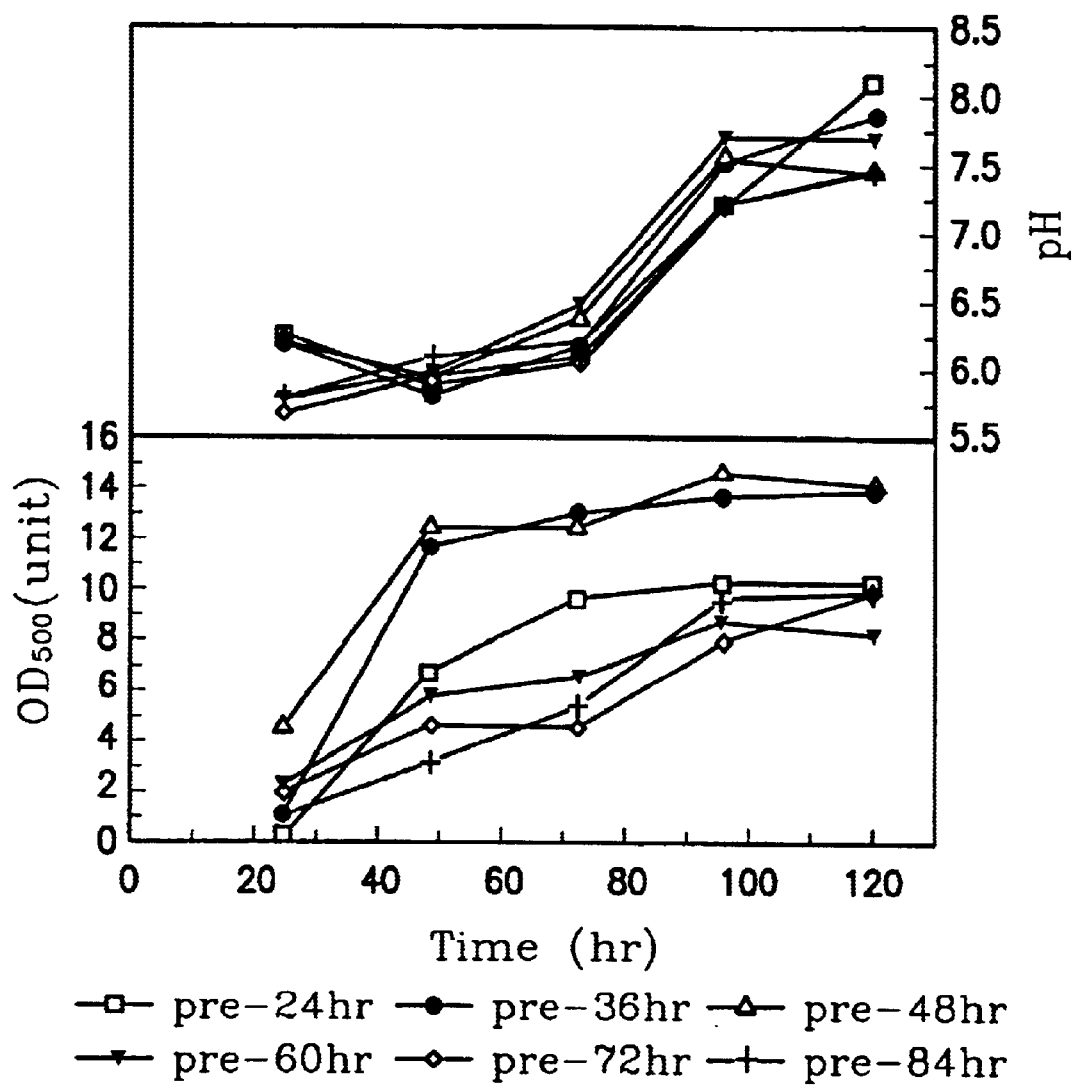
FIG. 2 is a diagram showing the effects of the cultivation of Monascus species and pigments produced using different periods of inoculum.

The shaken-flask cultivation was carried out by using medium A except only 2% rice particles were employed as the carbon source. The 24, 36, 48, 60, 72 and 84-hour-old inoculum was inoculated into 1 liter Erlenmeyer flask containing culture medium for shaken-flask cultivation. The result is shown in FIG. 2, wherein the 36 and 48-hour-old inoculum have better production of pigments (after cultivation for 50 hours, the absorbance of $OD_{500}$ can reach 12 units).

EXAMPLE 3
The Fluid Properties of the Pneumatic Bioreactor 3 types of pneumatic bioreactors (13 cm in diameter and 200 cm in height) were used to compare their fluid properties, namely: (1) a conventional bubble column bioreactor (without the draft tubes), also called bubble column for short; (2) an air-lift bioreactor (equipped with a draft tube, which was 100 cm high and 8.5 cm in diameter), also called air-lift for short; and (3) an air-lift bioreactor with double net draft tubes (equipped with a concentric double net draft tubes which were 100 cm high and respectively 6 cm and 8.5 cm in diameter, wherein the mesh number of the draft tubes was 3), also called net column for short. The two-phase system (air-water) and three-phase system (2% rice particle-air-water) were used herein as the fluid systems, respectively.

The properties of the bioreactor were evaluated in terms of transport phenomena, including (1) gas holdup; (2) oxygen mass transfer coefficient; and (3) liquid mixing time. The gas holdup, $\epsilon$, was measured by the volume expansion method. The oxygen mass transfer coefficient, $k_L a$, was determined by the dynamic method. The liquid mixing time was measured by dynamic heat-transfer method.

Result

Figure 3:
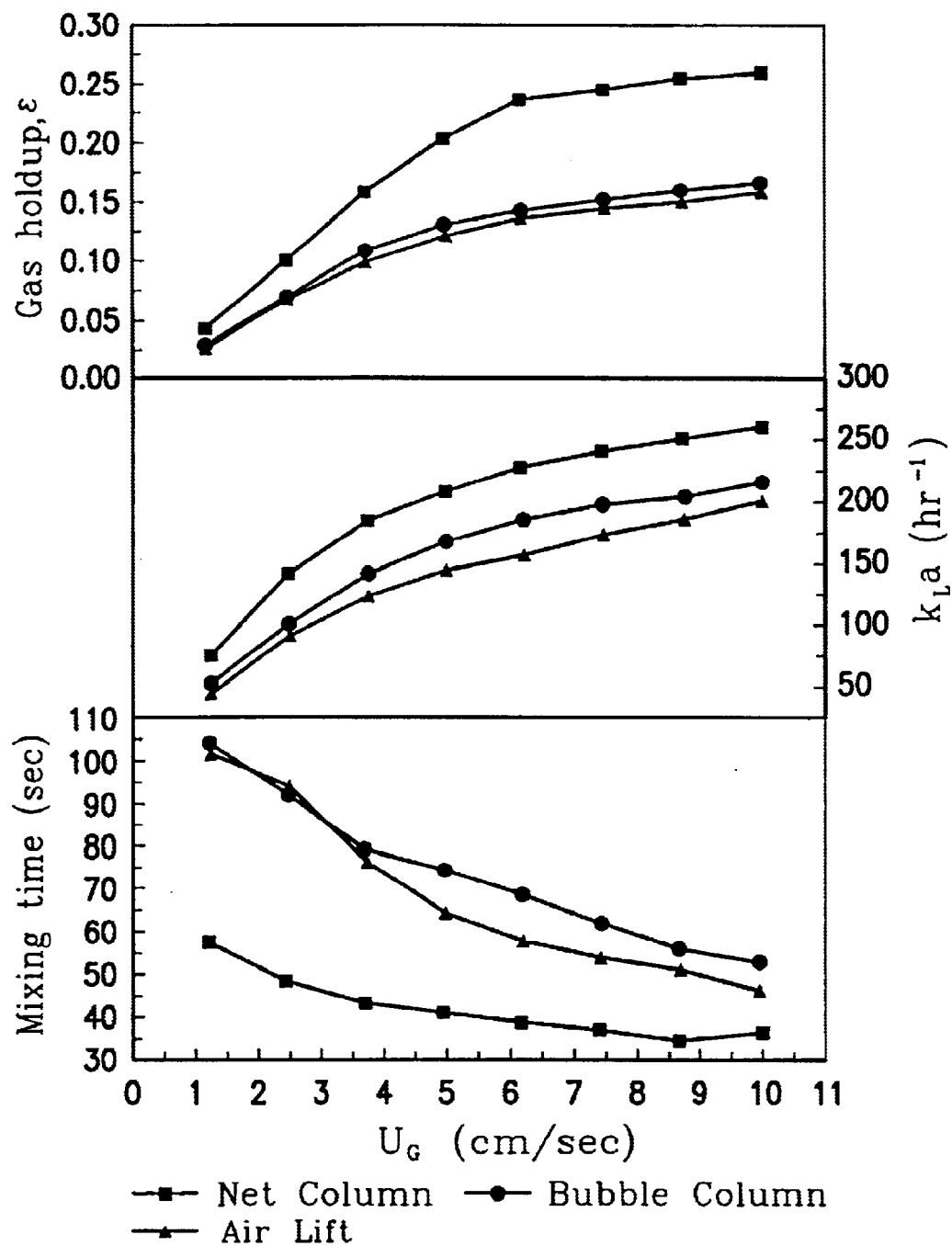
FIG. 3 is a diagram showing the fluid properties of a two-phase pneumatic bioreactor by using air-water as the fluid system, wherein the initial height of the liquid is 120 cm and the temperature is set at 30° C.
Figure 4:
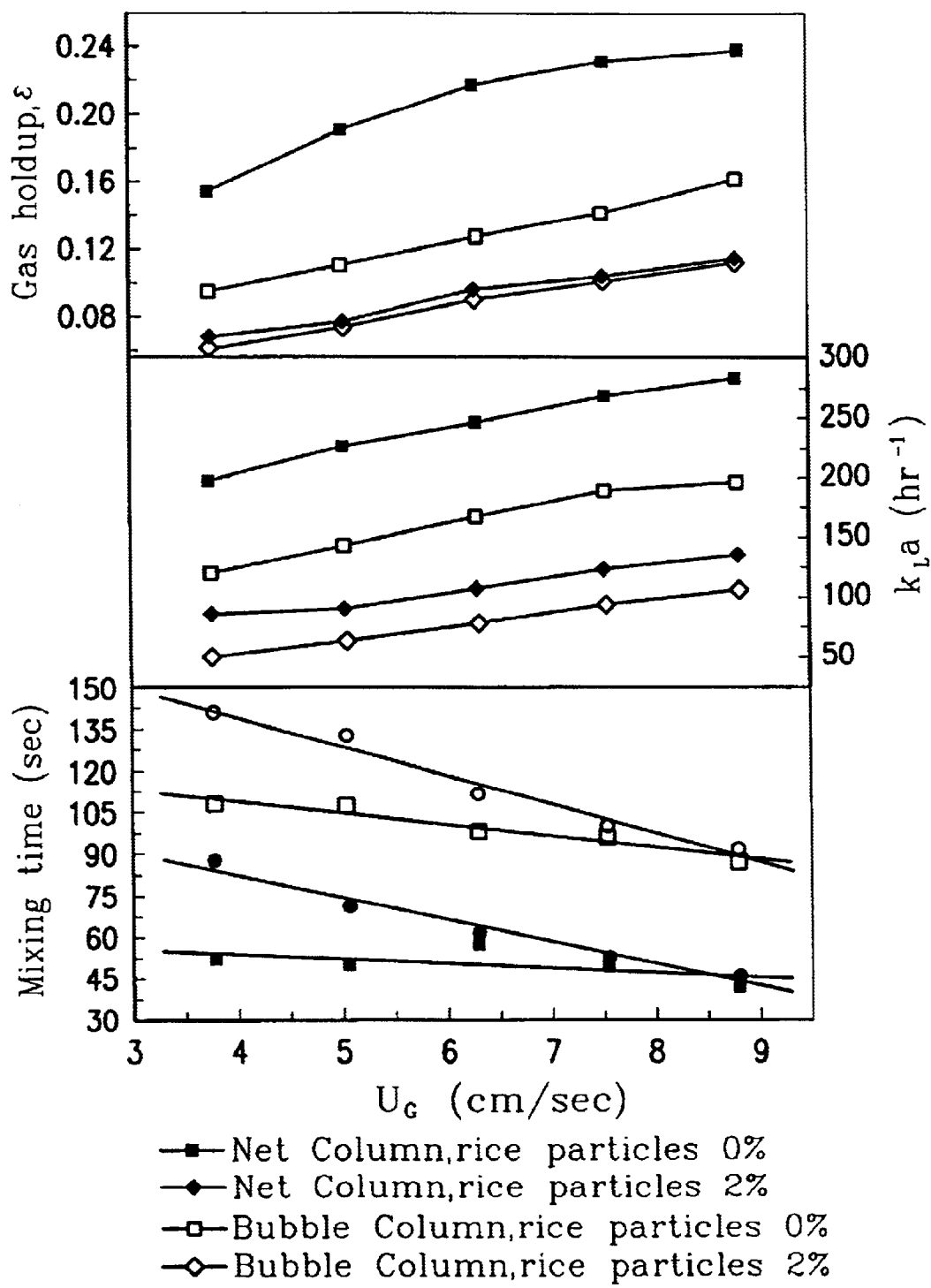
FIG. 4 is a diagram showing the fluid properties of three-phase pneumatic bioreactor by using 2% rice particle-air-water as the fluid system, wherein the initial height of the liquid is 120 cm and the temperature is set at 30° C.

Referring to FIGS. 3 and 4, the fluid properties of the air-lift bioreactor with net draft tubes are better. Generally, the solid particles contained in culture broth in the bubble column bioreactor will decrease gas holdup, oxygen mass transfer coefficient and liquid mixing time, and thus seriously affecting the efficiency of bioreactor.

After adding rice particles, all transport phenomena will be decreased whether in bubble column bioreactor or in air-lift bioreactor with net draft tubes. However, as shown in FIG. 4, the fluid properties of the air-lift bioreactor with net draft tubes are better than those of bubble column bioreactor. Thus, the air-lift bioreactor with net draft has less shear stress and is suitable for the fermentation of such aerobic microorganisms.

EXAMPLE 4

Cultivation of *M. purpureus* in Pneumatic Bioreactor

Figure 5:
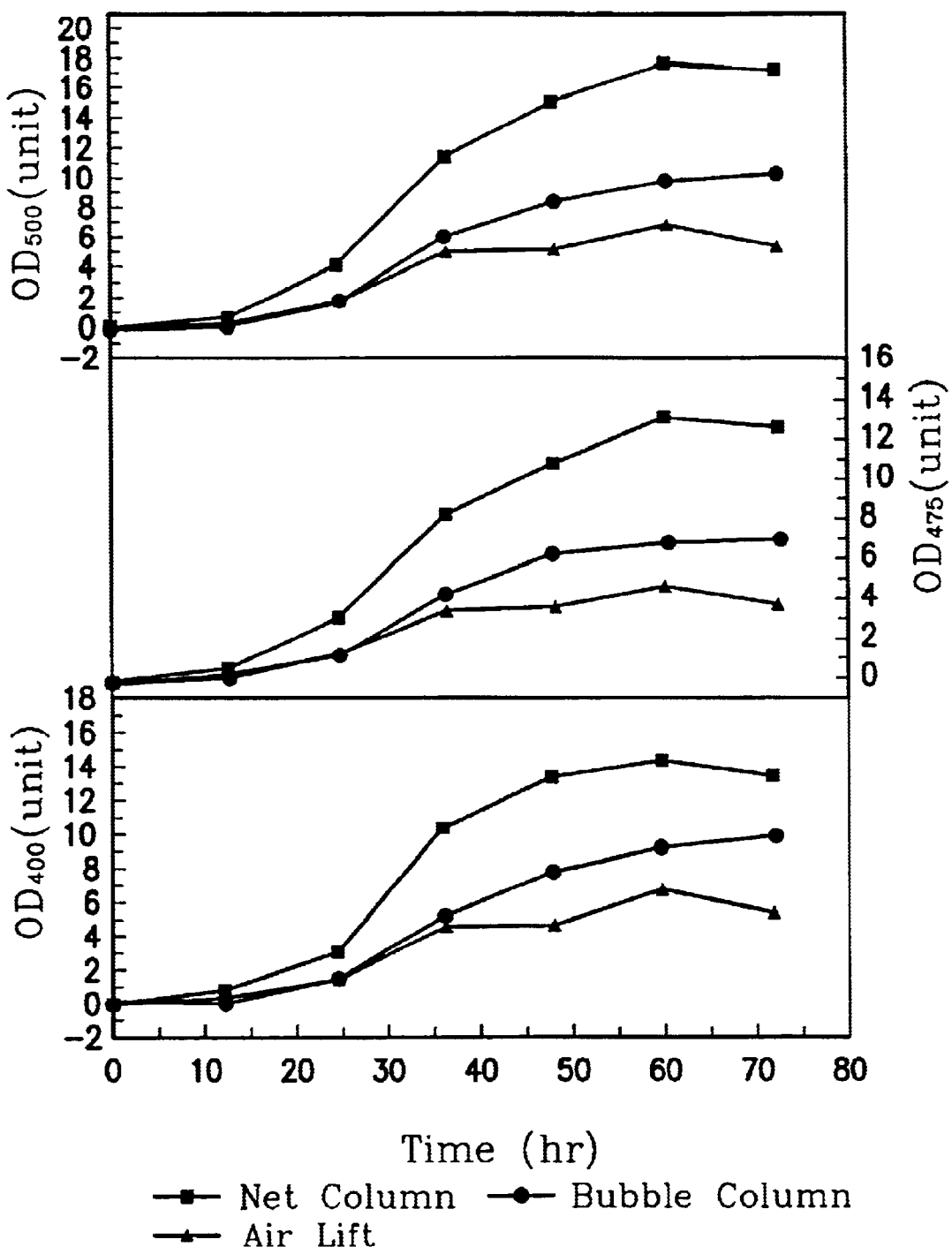
FIG. 5 is a diagram showing the production of Monascus pigments by using three different pneumatic bioreactors.

Batch culture of *M. purpureus* with suspended 2% rice particles was carried out in 3 types of pneumatic bioreactors to compare the yield of Monascus pigments. Cultivation was carried out with 15 liters culture medium at 30° C. under the aeration of 2 VVM (i.e. superficial air velocity of 3.768 cm/sec) and inoculated with 8.5% mycelium broth, which was 48-hour-old inoculum. The yield of pigments was evaluated by spectrophotometry (DU-530, Beckman Instruments, U.S.A.), including 500, 475 and 400 nm for red, orange and yellow pigments, respectively. The result is shown in FIG. 5.

Result

The yield of Monascus pigments in the air-lift bioreactor with net draft tubes is the best among the 3 types of pneumatic bioreactors tested. After cultivation for 60 hours, the absorbance of $OD_{500}$ can reach 18 units, which is also better than that in shaken-flask cultivation (refer to FIG. 1). It is observed that the yields of Monascus pigments in bubble column bioreactor and in air-lift bioreactor are not higher than those in shaken-flask cultivation. One reason is the small scale of shaken-flask cultivation (about 300 ml relative to 15 liters of broth in bioreactor); thus, gas is easily mixed with liquid by shaking. On the other hand, both the bubble column bioreactor and the air-lift bioreactor have the disadvantage of not mixing well after scale-up. The three-phase system of an air-lift bioreactor with net draft tubes according to the present invention has the advantages of better mixing, and thus is suitable for cultivation of filamentous fungi.

EXAMPLE 5

Figure 6:
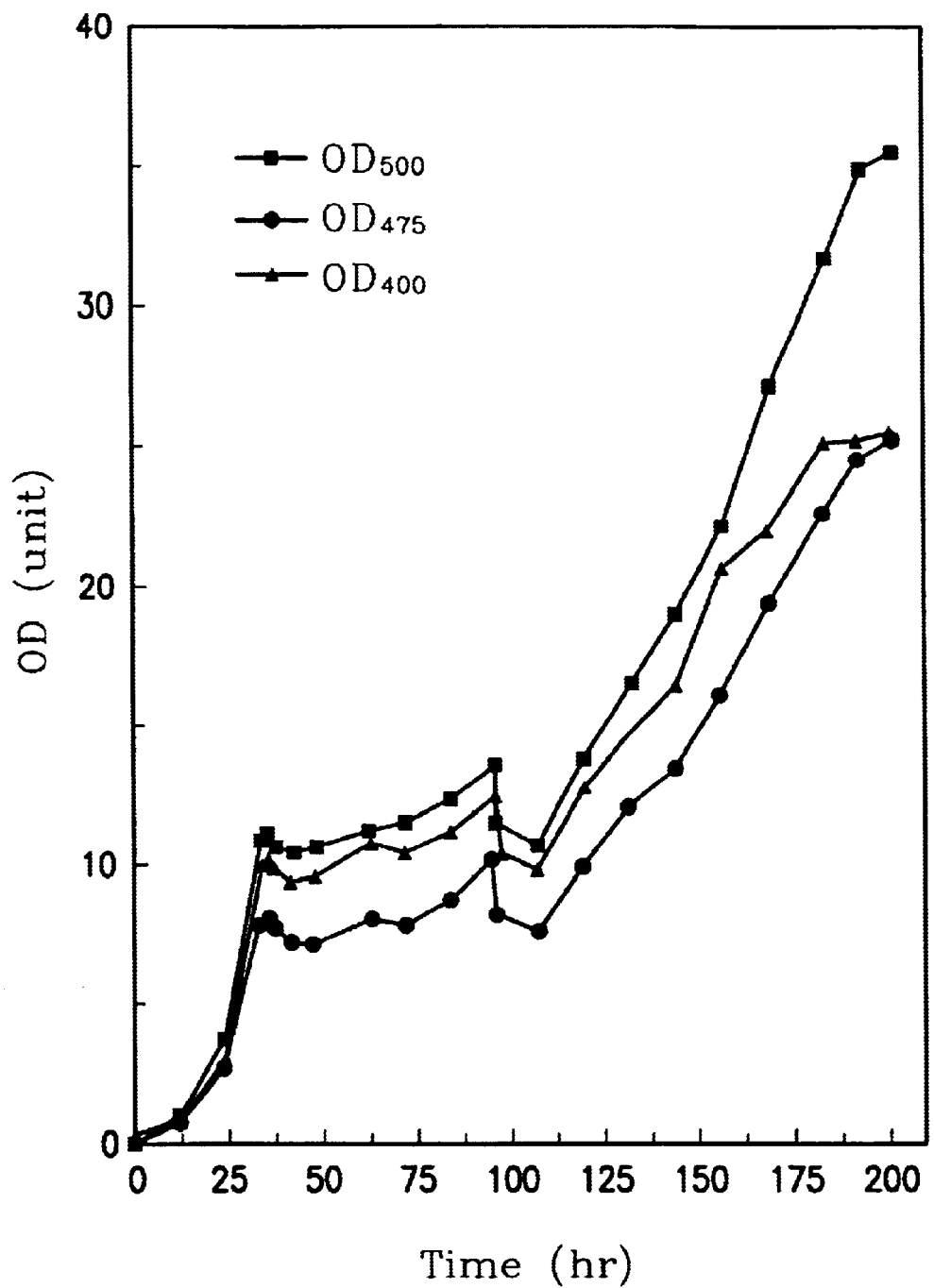
FIG. 6 is a diagram showing the production of Monascus pigments by using the process of fed-batch in an air-lift bioreactor with a net draft tube.

Fed-batch Cultivation of *M. purpureus* in Air-lift Bioreactor with Net Draft Tubes During the process of fermentation, the rice particles were broken down and destroyed due to the effects of mycelia penetration and shear stress, such that the content of rice particles were decreased. Thus, the fermentation broth was supplemented with the rice particles using the fed-batch process to maintain the three-phase fermentation system. The condition of the fermentation was the same as batch cultivation described in Example 4, and the medium used herein also contained 2% rice particles and 1.26% monosodium glutamate. The total culture time was 200 hours, and the medium was fed on the $35^{th}$ and $100^{th}$ hour. The result is shown in FIG. 6, revealing the absorbance of $OD_{500}$ can reach 36 units, which is 2 fold higher than that in batch cultivation.

The present invention improves the yield of metabolites such as Monascus pigments in submerged fermentation. It combines the characteristics of solid-state fermentation and submerged fermentation to achieve the properties of mycelia attachment and suspended fluidity, thereby solving the problems of scale-up and operation in solid-state fermentation. The present invention employs an air-lift bioreactor with a net draft tube to provide the dissolved oxygen required for the growth of cells and to avoid destroying mycelia and rice structure by the shear stress of the bioreactor. Moreover, the present invention also employs the fed-batch process to supplement the rice and nutrition consumed during the fermentation, thereby elevating the yield of Monascus pigments.

While the invention has been particularly shown and described with the reference to the preferred embodiment thereof, it will be understood by those skilled in the art that various changes in form and details may be made without departing from the spirit and scope of the invention.

What is claimed is:

1. A method for cultivation of filamentous fungi comprising the steps of:
    (a) preparing a medium for submerged culture comprising rice particles that receive said filamentous fungi, wherein the rice particles are husked, cooked, and sterilized before being added to said medium; and
    (b) inoculating said medium with said filamentous fungi in a bioreactor to carry out fermentation wherein the mycelia of said filamentous fungi are attached to said rice particles.

2. The method as claimed in claim 1, wherein said filamentous fungi comprise Monascus, Penicillium or Aspergilus.

3. The method as claimed in claim 1, wherein said medium in step (a) further comprises a nitrogen source, inorganic salts and trace elements.

4. The method as claimed in claim 1, wherein step (b) further comprises culturing said filamentous fungi prior to introduction into said medium.

5. The method as claimed in claim 4, wherein the culturing step comprises:
    (1) inoculating said filamentous fungi from a stock culture to a new agar plate and incubating in an incubator for 5 to 7 days;
    (2) washing spores and mycelia grown on said plate with sterile water; and
    (3) cultivating for about 36 to 48 hours said spores and mycelia in a medium comprising rice particles by shaking to form a culture.

6. The method as claimed in claim 1, wherein said bioreactor is a pneumatic bioreactor.

7. The method as claimed in claim 6, wherein said pneumatic bioreactor is an air-lift bioreactor with a net draft tube.

8. The method as claimed in claim 1, further comprising cultivating said filamentous fungi using the fed-batch process.

9. The method as claimed in claim 8, wherein the medium of the batch comprises a nitrogen source and rice particles.

10. A method for cultivation of the Monascus species comprising the steps of:
    (a) preparing a medium for submerged culture comprising rice particles that receives said Monascus species, wherein the rice particles are husked, cooked and sterilized before being added to said medium; and (h) inoculating said medium with said Monascus species in a bioreactor to carry out fermentation wherein the mycelia of said Monascus species are attached to said rice particles.

11. The method as claimed in claim 10, wherein step (b) further comprises culturing said Monascus species prior to introduction into said medium.

12. The method as claimed in claim 11, wherein the culturing comprises:

(1) inoculating said Monascus species from a stock culture to a new agar plate and incubating in an incubator for 5 to 7 days;

(2) washing spores and mycelia grown on said plate with sterile water; and (3) cultivating for about 36 to 48 hours said spores and mycelia in a medium comprising rice particles by shaking, to form a culture.

13. The method as claimed in claim 12, wherein said bioreactor is a pneumatic bioreactor.

14. The method as claimed in claim 13, wherein said pneumatic bioreactor is an air-lift bioreactor with a net draft tube.

15. The method as claimed in claim 10, further comprising cultivating said Monascus species using the fed-batch process.

16. The method as claimed in claim 15, wherein the medium of the batch comprises a nitrogen source and rice particles.

17. A method for producing metabolites from cultivation of the Monascus species comprising the steps of:

(a) preparing a medium for submerged culture comprising rice particles that receive said Monascus species, wherein the rice particles are husked, cooked, and sterilized before being added to said medium; and (b) inoculating said medium with said Monascus species in a bioreactor to carry out fermentation wherein the mycelia of said Monascus species are attached to said rice particles.

18. The method as claimed in claim 17, wherein step (b) further comprises culturing said Monascus species prior to introduction into said medium.

19. The method as claimed in claim 18, wherein the culturing comprises:

(1) inoculating said Monascus species from a stock culture to a new agar plate and incubating in an incubator for 5 to 7 days;

(2) washing spores and mycelia grown on said plate with sterile water; and (3) cultivating for about 36 to 48 hours said spores and mycelia in a medium comprising rice particles by shaking, to form a culture.

20. The method as claimed in claim 19, wherein said bioreactor is a pneumatic bioreactor.

21. The method as claimed in claim 20, wherein said pneumatic bioreactor is an air-lift bioreactor with a net draft tube.

22. The method as claimed in claim 17, further comprising cultivating said Monascus species using the fed-batch process.

23. The method as claimed in claim 22, wherein the medium of the batch comprises a nitrogen source and rice grain particles.

* * * * *